United States Patent [19] [11] 4,443,378
Günther [45] Apr. 17, 1984

[54] PROCESS FOR THE SEPARATION OF ACYLATED PHOSPHOLIPIDS FROM PHOSPHATIDYLCHOLINE PRODUCTS CONTAINING THE SAME

[75] Inventor: Bernd-Rainer Günther, Bergheim, Fed. Rep. of Germany

[73] Assignee: A. Nattermann & Cie GmbH, Cologne, Fed. Rep. of Germany

[21] Appl. No.: 326,326

[22] Filed: Dec. 1, 1981

[30] Foreign Application Priority Data

Dec. 13, 1980 [DE] Fed. Rep. of Germany ....... 3047012

[51] Int. Cl.$^3$ ............................ A23J 7/00; C07F 9/02; C11C 3/00
[52] U.S. Cl. ....................................................... 260/403
[58] Field of Search ........................................... 260/403

[56] References Cited

U.S. PATENT DOCUMENTS

| | | | |
|---|---|---|---|
| 3,031,478 | 4/1962 | Klenk et al. | 260/403 |
| 3,359,201 | 12/1967 | Eichberg | 260/403 |
| 3,704,254 | 11/1972 | Aneja | 260/403 |
| 3,752,833 | 8/1973 | Aneja et al. | 260/403 |
| 3,960,905 | 6/1976 | Eilb et al. | 260/403 |
| 3,985,875 | 10/1976 | Hayashi et al. | 260/403 X |
| 4,086,257 | 4/1978 | Sears | 260/403 |
| 4,130,571 | 12/1978 | Nakajima et al. | 260/403 |
| 4,163,748 | 8/1979 | Eibl et al. | 260/403 |
| 4,323,563 | 4/1982 | Takami et al. | 260/403 X |

FOREIGN PATENT DOCUMENTS

| | | |
|---|---|---|
| 1118373 | 7/1968 | United Kingdom . |
| 1174399 | 12/1969 | United Kingdom . |
| 1217846 | 12/1970 | United Kingdom . |

*Primary Examiner*—Helen M. S. Sneed
*Attorney, Agent, or Firm*—Pearne, Gordon, Sessions, McCoy, Granger & Tilberry

[57] ABSTRACT

The present invention is related to a new process for the separation of acylated phospholipids, in particular of acylated phosphatidylethanolamine and possibly oils from phosphatidylcholine products containing the same, by chromatography on silicic acid gel in a lower alkanol containing 1 to 4 carbon atoms as solvent and/or eluant yielding into highly purified phoshatidylcholine.

5 Claims, No Drawings

PROCESS FOR THE SEPARATION OF ACYLATED PHOSPHOLIPIDS FROM PHOSPHATIDYLCHOLINE PRODUCTS CONTAINING THE SAME

The present process is related to a new process for the separation of acylated phospholipids, in particular of acylated phosphatidylethanolamine, and possibly oils from phosphatidylcholine products containing the same, by chromatographic adsorption of silicic acid gel thus producing highly purified phosphatidylcholine.

There are traded phosphatidylcholine products containing acylated phospholipids, in particular acetylated phosphatidylethanolamine and which are used as emulgators (British Pat. Nos. 1,118,373 and 1,174,399). These products are produced by treating natural phosphatide mixtures containing phosphatidylethanolamine for instance with acetic acid anhydride at an elevated temperature (see for instance British Pat. No. 1,217,846, U.S. Pat. No. 3,752,833, U.S. Pat. No. 3,359,201, U.S. Pat. No. 3,704,254). However, acylation may also occur with other acylating agents.

Phosphatidylcholine is used to a great extent in the pharmaceutical industry. It is necessary to have for this purpose highly pure phosphatidylcholine. In particular it is necessary that the used phosphatidylcholine is separated from the mono-, di- and triglycerides (hereinafter referred to as oils) as well as acylated phosphatidylethanolamine and possibly present non-acylated phosphatidylethanolamine completely.

The acylation of natural phosphatide mixtures containing phosphatidylethanolamine already has been used for the separation of the oils and phosphatidylethanolamine (see Fett, Seifen, Anstrichmittel, vol. 73 (1971), pgs. 643 to 651). The fact is used for this separation that phosphatidylcholine and phosphatidylethanolamine are insoluble in acetone while the oils and acylated phosphatidylethanolamine are soluble in acetone thus allowing extraction of the oils and acetylated phosphatidylethanolamine from the insoluble phosphatidylcholine. The disadvantage of this process however is that acetone in these processes as known yields into small amounts of acetone derivatives such is mesityloxide, diacetone alcohol, phoron and others which products are toxic and therefor have to be separated from the phosphatidylcholine to be used in pharmaceutical industry. The separation of such acetone derivatives however is either most burdensome or even impossible. Furthermore, during such separation processes by means of acetone increase of peroxide formation occurs which have known undesirable physiological properties. A further disadvantage of this process is that the acetylation of phosphatidylethanolamine with acetic acid anhydride, due to the presence of a basic amino group and to formation of acetic acid during acetylation, is not complete because of salt formation of the amino group to an ammonium group. This does not allow full separation of the phosphatidylethanolamine. Furthermore, the separation of the other naturally occurring by-products of phosphatidylcholine is most burdensome.

It is an object of the present invention to produce a new simplified process for the separation of acetylated phospholipids such as acetylated phosphatidylethanolamine and possibly of present non-acylated phosphatidylethanolamine and/or oils from phosphatidylcholine crude products thus yielding into a highly purified phosphatidylcholine.

The process according to the present invention for the separation of acylated phospholipids and possibly of present non-acylated phospholipids and/or oils contained in naturally occurring phosphatidylcholine crude products is characterized in that the phosphatidylcholine product, possibly after separation from insoluble by-products, is dissolved in a lower alkanol having from 1 to 4 carbon atoms or a mixture of such alkanols, possibly containing up to 20% by volume of water, the resulting solution is put on to a chromatographic column of silicic acid gel at a temperature ranging from 60° to 90° C., this column is eluated at this temperature with a lower alkanol having from 1 to 4 carbon atoms or a mixture of several of such alkanols, that alkanol or mixture of alkanols containing up to 20% by volume of water, a preeluate containing the acylated phospholipide and possibly present non-acylated phospholipide and/or oils to be separated is collected and, separate therefrom, a main fraction containing the highly purified phosphatidylcholine is collected and the solvent is separated from the main eluate in usual manners.

Preferably, the solution is put on to the chromatographic silicic acid gel column and the elution of the column occurs at a temperature ranging from 60° to 70° C. Preferably the used solvent and eluant are identical which allows a particular simplification of the process. The preferred lower alkanol having from 1 to 4 carbon atoms is ethanol.

The amount of preeluate depends upon the phosphatidylcholine starting product. It may be simply determined by known analytical methods from which time of eluation the eluate is free of the by-products to be separated and practically only contains phosphatidylcholine. According to general experience with various phosphatidylcholine products and the application of the present process, the preeluate is about 20 to 25% of the total volume of the eluate. If desired, the solvent may also be separated from the preeluate and may be further used in known methods.

The silicic acid gel is a known product usual in chromatography having varying grain size. It furthermore can be pressed silicic acid gel. Such silicic acid gel products may be activated or deactivated. Most preferred are neutral silicic acid gel products.

The process according to the present invention may be carried out at normal pressure or at elevated pressures. It is a particular advantage of the process of the present invention that the silicic acid gel may repeatedly be used. All impurities are contained in the preeluate. After collection of the main eluate there is only adsorbed a small amount of phosphatidylcholine.

A further advantage of the silicic acid gel used in the present process is the high amount which can be adsorbed. Thus, carrying out the present process with 100 parts by weight of silicic acid gel about 60 parts by weight of solid material may be separated from the alcohol soluble phosphatide fraction.

The process according to the present process furthermore has the advantage that highly pure phosphatidylcholine may be produced if in the acylation step not all of the present phosphatidylethanolamine has been acylated and/or the product obtained from acylation still contains mono-, di- and triglycerides (oils). These by-products too may be completely separated by means of the process of the present invention and therefor are collected in the preeluate even without elongation of the time of elution for the preeluate.

EXAMPLES

Analysis

The phosphatides are analysed by thin layer chromatography. The oil content is equal the products which may be dialysed. The water content is determined according to Karl Fischer and the ethanol content is determined by gaschromatography.

Column chromatography

There is used a usual heatable column (inner diameter 4.5 cm., length 37 cm.). The column is combined with a heat exchanger in order to guarantee equal column temperature and starting temperature of the solution. The column is prepared from a slurry of 200 g. of silicic acid gel (Merck, Darmstadt/Germany) in the applied solvent. The silicic acid gel may be reused after used in the present process.

Starting materials

There is used as starting material a soybean phosphatide containing 20% of phosphatidylcholine (PC), 14% of phosphatidylethanolamine (PE) and 30% of oils.

EXAMPLE 1

400 g. of the soybean crude phosphatide are stirred with 24 g. of acetic acid anhydride for one hour at 50° C. The volatile components are distilled off in a vacuum in a rotatable evaporator. The residue is extracted with 800 g. of 95% ethanol at 50° C. The mixture is cooled to room temperature and the clear supernatant ethanol phase is separated. The ethanol is distilled off in a vacuum. The residue (92 g.) is analysed with the following result:

Phosphatidylcholine (PC): 40%
Phosphatidylethanolamine (PE): 1%
N-Acetyl-PE: 12%
Oils: 20%

EXAMPLE 2

The product of example 1 is subjected to column chromatography at 65° C. 90 g. of solid material are dissolved in 810 g. of 95% ethanol and put onto the column. Eluate: 95% ethanol to produce a total of 4 liters of eluate.

After collecting 1.4 liters of preeluate a total of 2.6 liters of main eluate are collected. The main eluate is evaporated to dryness and analysed:

Yield in solid material: 19% of the theoretical
PC content: 93%
PE content: <1%
N-Acetyl-PE content: <1%
Oil content: <1%
Yield in PC, calculated to the solid starting material: 44% of the theoretical.

What I claim is:

1. Process for the separation of acylated phospholipids from phosphatidylcholine products containing the same characterized in that the phosphatidyl starting material is dissolved in a lower alkanol having from 1 to 4 carbon atoms or a mixture of several such alkanols, said alkanol or mixture of alkanols possibly containing up to 20% by volume, possibly present insolubles are separated from said solution, said clear solution is put on to a chromatographic column of silicic acid gel at a temperature ranging from 60° to 90° C., said column is eluated at an elevated temperature within this range with a lower alkanol having from 1 to 4 carbon atoms or a mixture of several such lower alkanols, said alkanol or said mixture possibly containing up to 20% by volume of water, a preeluate containing the by-products to be separated is collected, thereafter, separate therefrom, the main eluate containing the pure phosphatidylcholine is collected and the solvent is separated from said main eluate.

2. Process according to claim 1 wherein the solution of the crude phosphatidylcholine product to the silicic acid gel column and the eluation of the column occurs at a temperature ranging from 60° to 70° C.

3. Process according to claim 1 or 2 characterized in that for solution of the crude phosphatidylcholine product and for the eluation of the column identical solvents are used.

4. Process according to claim 3 characterized in that the lower alkanol having from 1 to 4 carbon atoms is ethanol.

5. Process according to claim 1 characterized in that the lower alkanol having from 1 to 4 carbon atoms is ethanol.

* * * * *